(12) United States Patent
Bogart et al.

(10) Patent No.: US 8,517,073 B2
(45) Date of Patent: Aug. 27, 2013

(54) APPARATUS AND METHOD FOR JOINING SIMILAR OR DISSIMILAR SUTURE PRODUCTS

(75) Inventors: Michael Bogart, Milford, CT (US); Christopher F. Fishbein, Wolcott, CT (US); David S. Kirsch, Madison, CT (US); Gregg Krehel, Newtown, CT (US); Russell Pribanic, Milford, CT (US)

(73) Assignee: Covidien LP, Mansfield, MA (US)

( * ) Notice: Subject to any disclaimer, the term of this patent is extended or adjusted under 35 U.S.C. 154(b) by 385 days.

(21) Appl. No.: 12/791,501

(22) Filed: Jun. 1, 2010

(65) Prior Publication Data
US 2011/0015653 A1 Jan. 20, 2011

Related U.S. Application Data

(60) Provisional application No. 61/226,018, filed on Jul. 16, 2009.

(51) Int. Cl.
*B32B 37/00* (2006.01)

(52) U.S. Cl.
USPC ......... 156/499; 156/502; 156/580.1; 606/232

(58) Field of Classification Search
USPC ................ 156/502, 580, 580.1, 580.2, 581, 156/499; 606/226, 228, 232
See application file for complete search history.

(56) References Cited

U.S. PATENT DOCUMENTS

| | | | |
|---|---|---|---|
| 2,591,063 A | 4/1952 | Goldberg | |
| 3,035,583 A | 5/1962 | Hirsch et al. | |
| 3,123,077 A | 3/1964 | Alcamo | |
| 3,311,110 A * | 3/1967 | Singerman et al. | 606/226 |
| 4,469,101 A | 9/1984 | Coleman et al. | |
| 4,516,584 A | 5/1985 | Garcia | |
| 4,553,961 A | 11/1985 | Pohndorf et al. | |
| 4,683,895 A | 8/1987 | Pohndorf | |

(Continued)

FOREIGN PATENT DOCUMENTS

| | | |
|---|---|---|
| EP | 0444777 A1 | 9/1991 |
| EP | 0490143 A2 | 6/1992 |

(Continued)

OTHER PUBLICATIONS

European Search Report for EP 10251270.4-2310 date of completion is Dec. 16, 2010 (4 pages).

(Continued)

*Primary Examiner* — James Sells

(57) ABSTRACT

An apparatus, system and method for joining a first length of suture with a second length of suture are provided. The apparatus includes a substantially cylindrical body have a first end and a second end, a first cavity formed in the first end for receiving an end of the first length of suture, and a second cavity formed in the second end for receiving an end of the second length of suture, wherein the ends of the first and second lengths of sutures are welded within respective first and second cavities. The first and second lengths of suture may include the same or different diameters. The first and second cavities may be separated by a divider, or instead, may be continuous. The end of the first length of suture may abut the end of the second length of suture within the cylindrical body.

16 Claims, 6 Drawing Sheets

(56) References Cited

U.S. PATENT DOCUMENTS

| | | | |
|---|---|---|---|
| 4,946,467 A | 8/1990 | Ohi et al. |
| 5,036,862 A | 8/1991 | Pohndorf |
| 5,041,128 A | 8/1991 | Korthoff |
| 5,041,129 A | 8/1991 | Hayhurst et al. |
| 5,051,107 A | 9/1991 | Korthoff |
| 5,059,212 A | 10/1991 | Korthoff |
| 5,059,213 A | 10/1991 | Chesterfield et al. |
| 5,067,959 A | 11/1991 | Korthoff |
| 5,078,731 A | 1/1992 | Hayhurst |
| 5,089,010 A | 2/1992 | Korthoff |
| 5,089,011 A | 2/1992 | Korthoff |
| 5,107,856 A | 4/1992 | Kristiansen et al. |
| 5,116,358 A | 5/1992 | Granger |
| 5,123,911 A * | 6/1992 | Granger et al. ............... 606/224 |
| 5,129,405 A | 7/1992 | Milijasevic et al. |
| 5,156,615 A | 10/1992 | Korthoff et al. |
| 5,224,955 A | 7/1993 | West |
| 5,226,912 A | 7/1993 | Kaplan et al. |
| 5,259,845 A | 11/1993 | Korthoff |
| 5,527,324 A | 6/1996 | Krantz et al. |
| 5,556,428 A | 9/1996 | Shah |
| 5,569,302 A | 10/1996 | Proto et al. |
| 5,626,611 A | 5/1997 | Liu et al. |
| 5,669,935 A | 9/1997 | Rosenman et al. |
| 5,735,877 A | 4/1998 | Pagedas |
| 5,741,281 A | 4/1998 | Martin |
| 5,741,301 A | 4/1998 | Pagedas |
| 5,865,836 A | 2/1999 | Miller |
| 6,296,659 B1 | 10/2001 | Foerster |
| 6,358,271 B1 | 3/2002 | Egan et al. |
| 6,368,343 B1 | 4/2002 | Bonutti et al. |
| 6,409,743 B1 | 6/2002 | Fenton, Jr. |
| 6,475,230 B1 | 11/2002 | Bonutti et al. |
| 6,508,829 B1 | 1/2003 | Levinson et al. |
| 6,511,498 B1 | 1/2003 | Fumex |
| 6,626,919 B1 | 9/2003 | Swanstrom |
| 7,150,757 B2 | 12/2006 | Fallin et al. |
| 7,218,972 B2 | 5/2007 | Rodriguez |
| 7,357,810 B2 | 4/2008 | Koyfman et al. |
| 2002/0029066 A1 | 3/2002 | Foerster |
| 2003/0065339 A1 | 4/2003 | Snyder et al. |
| 2003/0153948 A1 | 8/2003 | Morrison et al. |
| 2003/0204205 A1 | 10/2003 | Sauer et al. |
| 2004/0087981 A1 | 5/2004 | Berube et al. |
| 2004/0097983 A1 | 5/2004 | Snyder et al. |
| 2004/0162579 A1 | 8/2004 | Foerster |
| 2004/0199208 A1 | 10/2004 | Foerster |
| 2005/0085833 A1 | 4/2005 | Gedebou |
| 2006/0009789 A1 | 1/2006 | Gambale et al. |
| 2006/0084940 A1 | 4/2006 | Olsen et al. |
| 2007/0282355 A1 | 12/2007 | Brown et al. |
| 2008/0086152 A1 | 4/2008 | McKay et al. |
| 2008/0097524 A1 | 4/2008 | Goransson et al. |
| 2008/0154286 A1 | 6/2008 | Abbott |
| 2010/0160961 A1 | 6/2010 | Nawrocki |

FOREIGN PATENT DOCUMENTS

| | | |
|---|---|---|
| EP | 2 108 316 | 10/2009 |
| WO | WO0030550 A1 | 6/2000 |
| WO | WO02/080780 | 10/2002 |
| WO | WO 2005/087113 A1 | 9/2005 |

OTHER PUBLICATIONS

European Search Report for EP 10251270.4-2310 date of completion is Feb. 1, 2012 (4 pages).

European Search Report EP 11 25 0772, Feb. 1, 2012.

* cited by examiner

APPARATUS AND METHOD FOR JOINING SIMILAR OR DISSIMILAR SUTURE PRODUCTS

CROSS-REFERENCE TO RELATED APPLICATION

The present application claims the benefit of and priority to U.S. Provisional Patent Application Ser. No. 61/226,018, filed Jul. 16, 2009, the disclosure of which is herein incorporated by reference in its entirety.

BACKGROUND

1. Technical Field

The present disclosure relates to sutures used in surgical procedures. More particularly, the present disclosure relates to apparatus and methods for joining similar and dissimilar lengths of suture.

2. Background of Related Art

Myriad of variously configured sutures composed of countless materials are known, as are limitless procedures performed using the same. During the course of some of these procedures, it may be necessary to have a suture with a more flexible region along at least a portion of its length. The region of greater flexibility may help better navigate the suture through tissue or to a surgical site. A suture having a more flexible region may also be better suited to sew or gather tissue. A suture having dual or multiple flexibility may be necessary for use with a surgical stitching device where a more flexible section of suture is required immediately distal of the device.

Therefore, it would be beneficial to have an apparatus and method of joining two lengths of similar or dissimilar suture products.

SUMMARY

Accordingly, an apparatus for joining a first length of suture with a second length of suture is provided. The apparatus includes a substantially cylindrical body have a first end and a second end, a first cavity formed in the first end for receiving an end of the first length of suture, and a second cavity formed in the second end for receiving an end of the second length of suture, wherein the ends of the first and second lengths of suture are welded within respective first and second cavities. The first and second lengths of suture may include the same or different diameters. The first and second cavities may be separated by a divider, or instead, may be continuous. The end of the first length of suture may abut the end of the second length of suture within the cylindrical body.

In one embodiment, the first and second lengths of sutures are welded within the respective first and second cavities using one of contact heating, radiant heating or ultrasonic welding. The cylindrical body may be configured to be compressed about the ends of first and second lengths of suture received within the respective first and second cavities. The cylindrical body may include barbs extending into at least one of the first and second cavities configured to more securely retain the ends of the first and second lengths of suture therein.

Also provided is a method of joining a first length of suture and a second length of suture. The method including providing a ferrule including a substantially cylindrical body having a first end defining a first cavity and a second end defining a second cavity, wherein the first and second cavities are configured to receive ends of respective first and second lengths of suture, inserting the end of a first length of suture within the first cavity and an end of a second length of suture within the second cavity, and applying energy to the ferrule to weld the ends of the first and second lengths of suture thereto. The step of applying energy to the ferrule may be accomplished using one of contact heating, radiant heating or ultrasonic welding.

Additionally provided is method of ultrasonically welding a first monofilament length of suture to a second multifilament length of suture. The method includes the steps of inserting a first end of a monofilament length suture into a first end of a multifilament length of suture to form an overlapping section of the first and second lengths of suture, and applying ultrasonic energy to the overlapping section of first and second sutures. The method may further include a step of providing a ferrule about the overlapping sections of the ends of the monofilament and multifilament second lengths of suture.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Apparatus and methods for joining lengths of suture will now be described with reference to the following figures. It should be understood that a length of suture, for purposes of this disclosure, is a portion of a suture, and that two lengths of suture may be combined according to methods of the present disclosure to create a single suture. The suture created by joining two lengths of suture may further have a needle affixed to at least one end thereof. Referring initially to FIGS.

1 and 2, a suture joining ferrule according to an embodiment of the present disclosure is shown generally as ferrule 20. Ferrule 20 is shown joining a length of a first suture 10 to a length of a second suture 30. As shown, first length of suture 10 is a monofilament thread while second length of suture 30 is a multifilament thread, however, first and second lengths of sutures 10, 20 may both be monofilament or multifilament.

Figure 1:
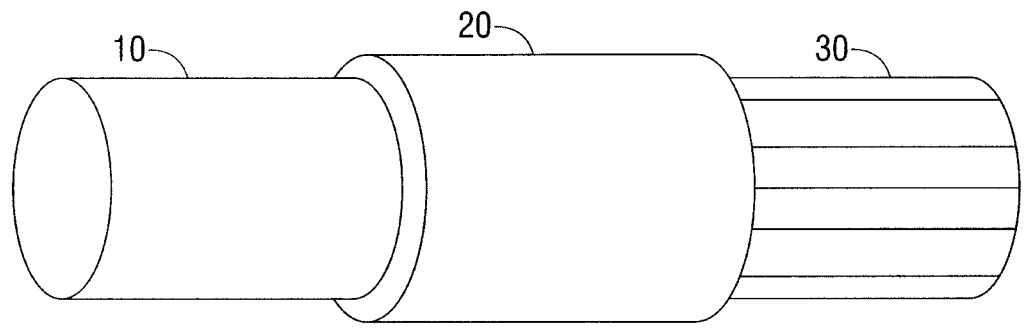
FIG. 1 is a perspective view of a first length of suture joined to a second length of suture using a ferrule according to an embodiment of the present disclosure.
Figure 2:
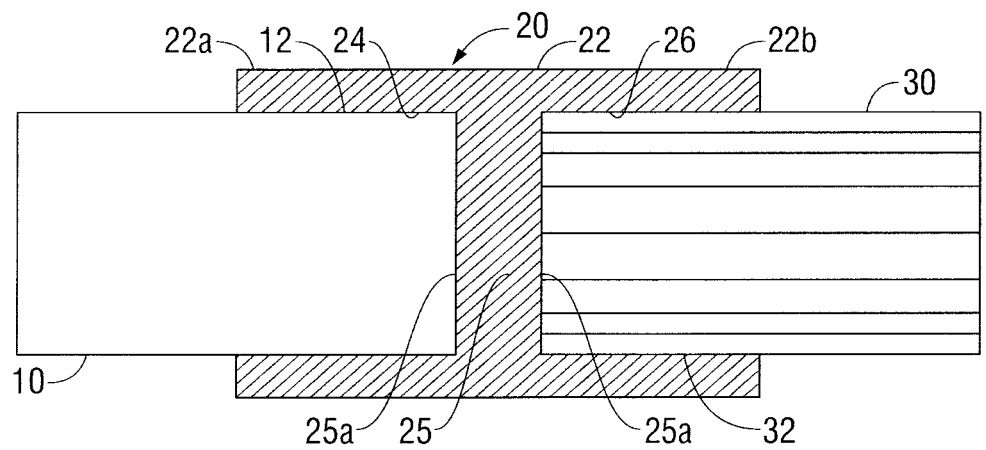
FIG. 2 is a partial cross-sectional view of the ferrule and sutures combination of FIG. 1.

Still referring to FIGS. 1 and 2, either or both of first and second lengths of suture 10, 30 may be formed of degradable materials, non-degradable materials, or combinations thereof. More particularly, either or both of suture lengths 10, 30 may be formed of a degradable material selected from the group consisting of polyesters (e.g., glycolide, lactide), polyorthoesters, polymer drugs, polyhydroxybutyrates, proteins, catgut, collagens, carbonates (e.g., trimethylene, tetramethylene), caprolactone, dioxanone, homopolymers thereof, copolymers thereof, and combinations thereof. In some embodiments, glycolide and lactide based polyesters, especially copolymers of glycolide and lactide, may be utilized to form either or both of sutures 10, 30.

Suitable non-degradable materials which may be utilized to form either or both of first and second lengths of suture 10, 30 include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, collagen, cotton, linen, carbon fibers, and the like. The polypropylene may be isotactic polypropylene or a mixture of isotactic and syndiotactic or atactic polypropylene.

First and second lengths of suture 10, 30 are formed using any technique within the purview of those skilled in the art, such as, for example, extrusion, gel-spinning, molding and/or solvent casting. In some embodiments, either or both of suture lengths 10, 30 may include a yarn made of more than one filament, which may contain multiple filaments of the same or different materials. Where either or both of suture lengths 10, 30 is made of multiple filaments, lengths of suture 10, 30 may be made using any known technique such as, for example, braiding, weaving or knitting. Either or both of suture lengths 10, 30 may also be combined to produce a non-woven suture. Either or both of suture lengths 10, 30 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

Figure 2A:
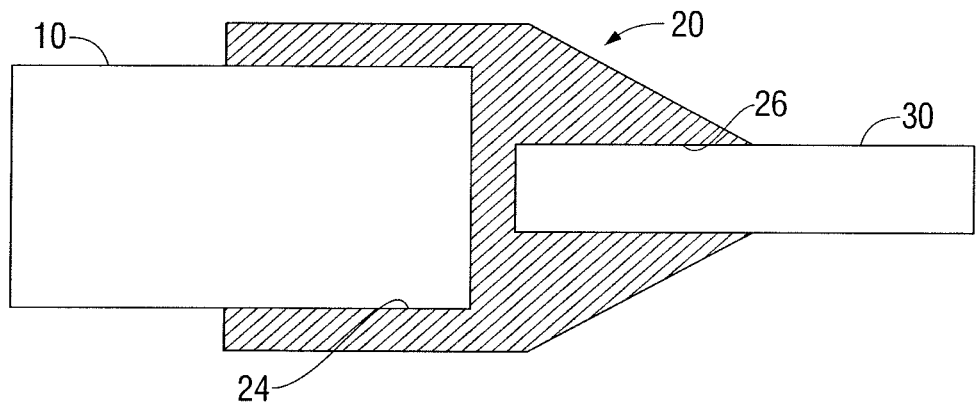
FIG. 2A is a partial cross-sectional view of an alternate embodiment of the ferrule of FIG. 1.
Figure 2B:
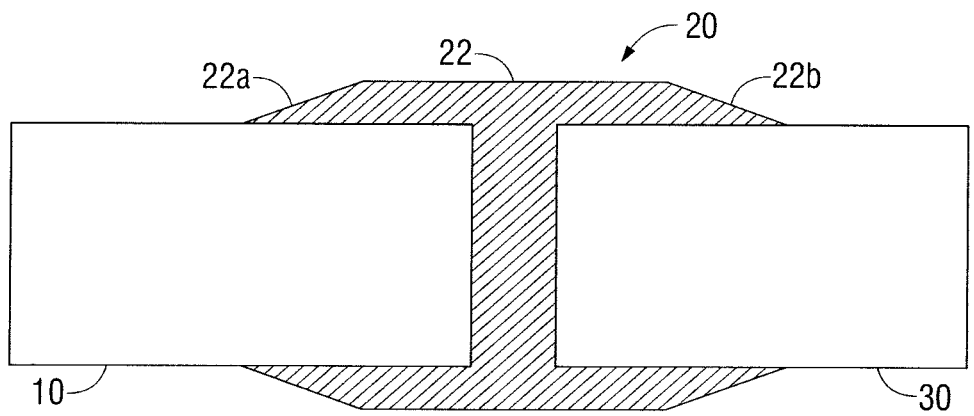
FIG. 2B is a partial cross-sectional view of another embodiment of the ferrule of FIG. 1.

Still referring to FIGS. 1 and 2, ferrule 20 may comprise plastics or other polymers, stainless steel, or other suitable materials. In some embodiments, ferrule 20 is bioabsorbable. As shown, ferrule 20 includes a substantially cylindrical member 22 defining an open first end 22a and an open second end 22b. First end 22a of ferrule 20 defines a first cavity 24 configured to receive an end 12 of first suture length 10. Second end 22b of ferrule 20 defines a second cavity 26 configured to receive an end 32 of second suture length 30. Each of first and second cavities 24, 26 may be of the same size, as shown in FIG. 2, to accommodate first and second lengths of suture 10, 30 having similar diameters. In alternative embodiments, first and second cavities 24, 26 may be of differing sizes (see, for example, FIG. 2A) to accommodated first and second lengths of suture 10, 30 of different sizes. Although shown having a circular cross-sectional geometry, the cross-sectional geometry of ferrule 20 and/or first and second cavities 24, 26 may be configured to accommodate suture lengths 10, 30 of any cross-sectional geometry. For example, either or both of suture lengths 10, 30 may have a round, elliptical, square, flat, octagonal, and rectangular cross-sectional geometry. First and second ends 22a, 22b of ferrule 20 may be tapered (FIG. 2B) or otherwise configured to lessen the transition between first suture length 10 and first end 22a of ferrule 20 and second suture length 30 and second end 22b of ferrule 20. In this manner, the combination of suture lengths 10, 30 may be more easily received through tissue.

Figure 2C:
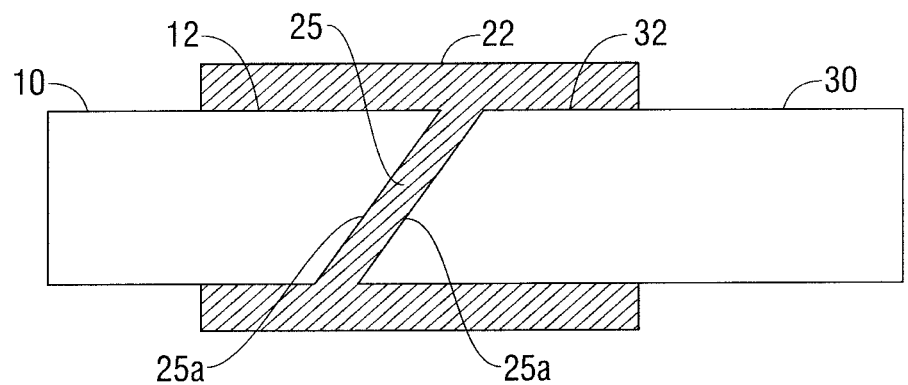
FIG. 2C is a partial cross-sectional view of still another embodiment of the ferrule of FIG. 1.
Figure 2D:
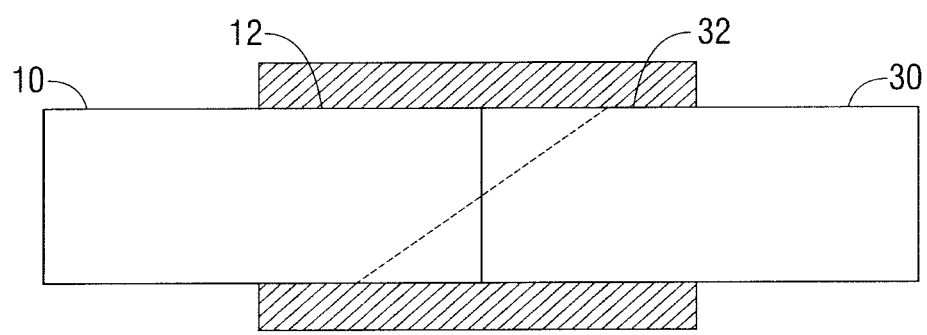
FIG. 2D is a partial cross-sectional view of still yet another embodiment of the ferrule of FIG. 1.

With reference still to FIG. 2, first and second cavities 24, 26 of ferrule 20 are separated by a divider 25 which provides structural support to ferrule 20. Divider 25 may have orthogonal walls 25a, as shown, or instead, either or both of walls 25a may be angled or tapered (FIG. 2C) to increase the surface area between either or both of first and second lengths of suture 10, 30 and ferrule 20. Ends 12, 32 of first and second lengths of suture 10, 30, respectively, may require shaping to lay flush against respective walls 25a. In an alternative embodiment, and as seen in FIG. 2D, first and second cavities 24, 26 are continuous and do not include a divider therebetween. Depending on the configuration of ferrule 20, ends 12, 32 of respective first and second lengths of suture 10, 30 may abut or overlap one another within ferrule 20.

First and second suture lengths 10, 30 are secured within ferrule 20 utilizing various welding methods, such as, for example, contact heating, radiant heating and ultrasonic welding. In one method, first and second suture lengths 10, 30 are welded within respective first and second cavities 24, 26 of ferrule 20 at the same time using a welding system, as will be discussed in detail below. Using an alternate method, first and second sutures 10, 30 are independently welded within respective first and second cavities 24, 26 of ferrule 20. In this manner, one of first and second lengths of suture 10, 30 is welded to and/or within ferrule 20 prior to the other of first and second lengths of suture 10, 30 being welded to and/or within ferrule 20. Either or both of first and second lengths of suture 10, 30 may be welded within ferrule 20 during manufacture or by a clinician prior to use. During the joining of first and/or second lengths of suture 10, 30 with ferrule 20, the heat created by the welding process may cause either or both of first and second lengths of suture 10, 30 to become integrally formed with each other and/or ferrule 20. Alternatively, or additionally, ferrule 20 may be constructed of a shapable and/or heat shrinkable material such that during the welding process, ferrule 20 may flex or constrict about respective suture ends 12, 32 of first and second lengths of suture 10, 30 such that each of cavities 24, 26 deforms to more securely receive respective suture ends 12, 32 therein.

Figure 2E:
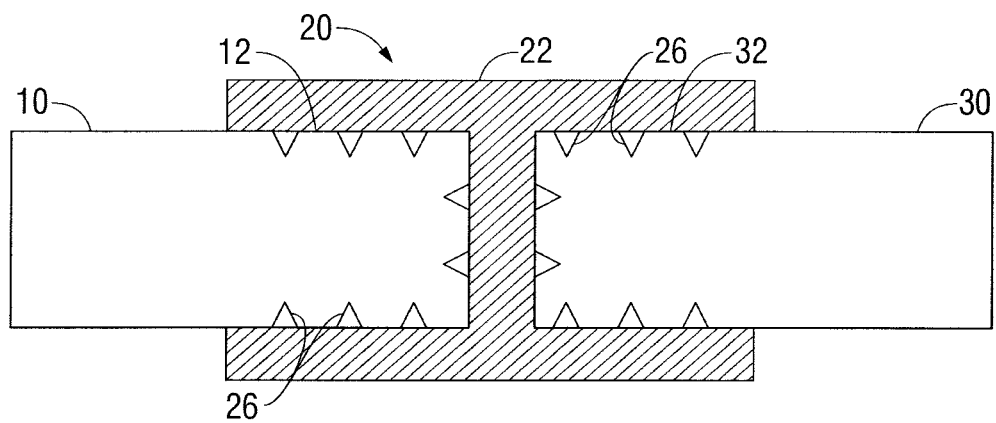
FIG. 2E is a partial cross-sectional view of yet another embodiment of the ferrule of FIG. 1.

A coating may be applied to either or both of suture lengths 10, 30 and/or either or both of cavities 24, 26 prior to inserting first suture length 10 within first cavity 24 and second suture length 30 within second cavity 26 to more securely join first and second suture lengths 10, 30 with ferrule 20. Alternatively, or in addition, either or both of suture lengths 10, 30 and/or either or both of cavities 24, 26 may be textured or otherwise surfaced prior to inserting first suture length 10 within first cavity 24 and second suture length 30 within second cavity 26 to more securely join first and second lengths of suture 10, 30 with ferrule 20. Either or both of suture lengths 10, 30 and/or either or both of cavities 24, 26 may include barbs 26 (FIG. 2E), prongs or other suitable structure configured to more securely retain respective first and second lengths of suture 10, 30 therein.

Figure 3:
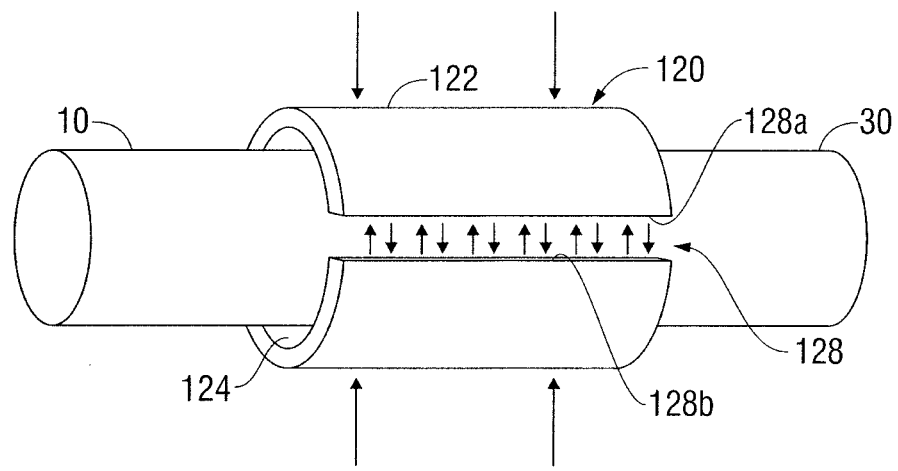
FIG. 3 is a perspective view of a first length of suture prior to being joined with a second length of suture using another embodiment of a ferrule according to the present disclosure.

With reference now to FIG. 3, an alternate embodiment of a ferrule according to the present disclosure is shown generally as ferrule 120. Ferrule 120 is substantially similar to ferrule 20 described hereinabove. Ferrule 120 includes a substantially cylindrical body 122 having a longitudinal gap 128 extending along the length thereof. Ferrule 120 defines a cavity 124 configured to receive an end of each of first and second lengths of suture 10, 30. Ferrule 120 is configured to be compressed or deformed about first and second lengths of suture 10, 30. In this manner, longitudinal gap 128 is narrowed or closed completely during the welding process. A first and second edge 128a, 128b which define gap 128 may be welded together to more securely retain first and second suture lengths 10, 30 within cavity 124.

Figure 4A:
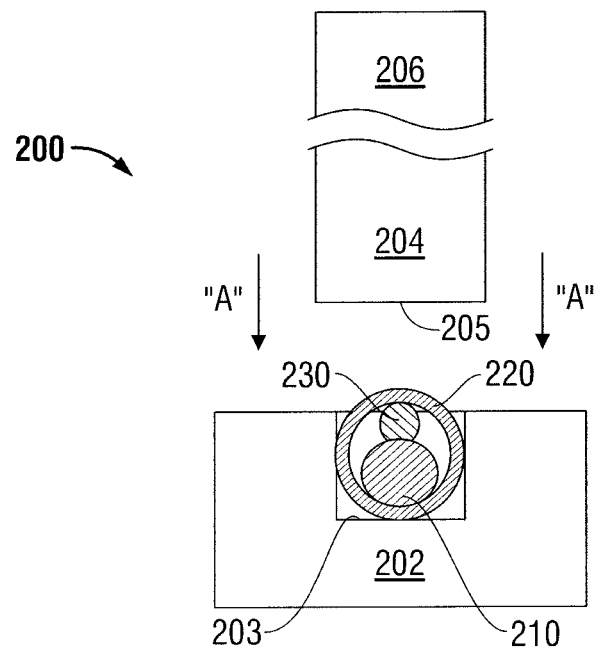
FIG. 4A is a cross-sectional end view of a ferrule and sutures combination according to the present disclosure prior to being joined by a first system for securing the first suture to the second suture.
Figure 4B:
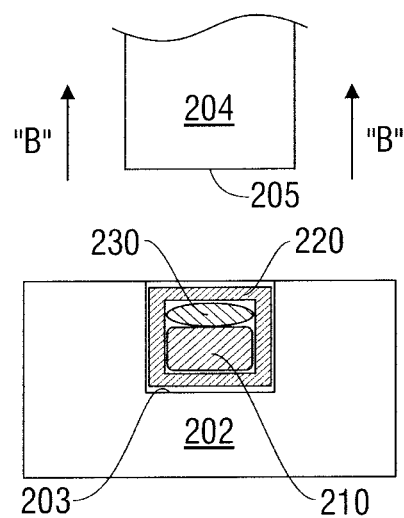
FIG. 4B is a cross-sectional end view of the ferrules and sutures combination of FIG. 4A after the first and second sutures have been joined by the first system.

With reference now to FIGS. 4A and 4B, a system and method for joining first and second lengths of suture 210, 230 is shown generally as suture joining system 200. Suture joining system 200 includes a base 202 and a die 204 operably connected to a source of energy 206. As discussed above with reference to ferrules 20, 120, first and second lengths of suture 210, 230 may be joined to ferrule 220 utilizing various welding methods, such as, for example, contact heating, radiant heating or ultrasonic energy. In an alternative embodiment, base 202 may instead, or also, be operably connected to the same or to a different source of energy 206.

Still referring to FIGS. 4A and 4B, base 202 includes a recess 203 configured to receive a ferrule 220 including an end 212 of a first length of suture 210 and an end 232 of a second length of suture 230. Recess 203 may be configured to partially or completely retain the ferrule and suture length combination. Recess 203 may include a rectangular profile, as shown, or instead may include a circular, rectangular, oval or other suitable shaped profile which may contour the geometry of the structure to be welded. Die 204 includes a ferrule contacting surface 205. As shown, ferrule contacting surface 205 is flat. Die 204 is configured to be approximated toward and away from base 202.

The operation of system 200 will now be described with reference to FIGS. 4A and 4B, initially, an end of first length of suture 210 and an end of a second length of suture 230 are received within a ferrule 120. Alternatively, ferrule 220 may be replaced by a sheath, either independently applied over first and/or second lengths of suture 210, 230, or provided with either first or second length of suture 210, 230. The combination of first and second lengths of suture 210, 230 and ferrule 220 is then received within recess 203 of a base 202.

Die 204 is then approximated towards base 202, in the direction of arrows "A". Conversely base 202 may be approximated toward die 204 and/or both die 204 and base 202 may be approximated toward each other. Prior to or upon engagement of die 204 with ferrule 220, energy source 206 is activated to cause the heating of die 204 and/or base 202. Contact of die 204 with ferrule 220 cause the joining of first and second lengths of suture 210, 230 with ferrule 220. As discussed above, first and second lengths of suture 210, 230 may be joined with ferrule 120 simultaneously, with one stroke of die 204, or individually, with two separate strokes of die 204. Alternatively, system 200 may include two dies 204 for independently welding first and second lengths of suture 210, 230 and ferrule 220.

As die 104 engages ferrule 220, ferrule 220 and first and second lengths of suture 210, 230, therein may be deformed to match the shape of recess 203. The deformation of ferrule 220 and first and second lengths of suture 210, 230 further secures suture lengths 210, 230 within ferrule 220. Approximation of die 204 away from base 202, in the direction of arrows "B", permits the release of newly joined first and second suture lengths 210, 230 from within recess 203 of base 202.

Figure 5A:
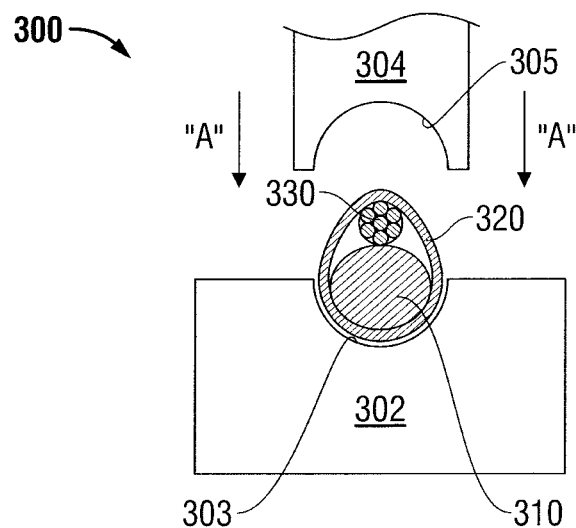
FIG. 5A is a cross-sectional end view of an alternate embodiment of a ferrule and sutures combination according to the present disclosure prior to being joined by a second system for securing the first suture to the second suture.
Figure 5B:
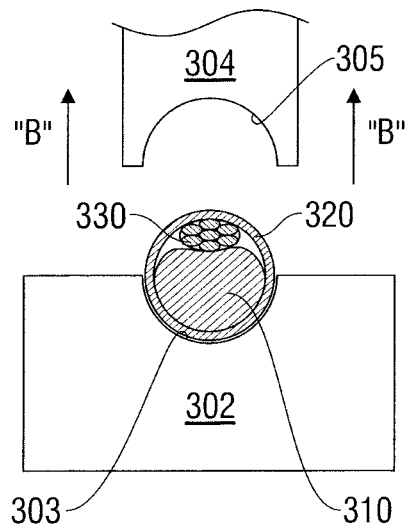
FIG. 5B is a cross-sectional end view of the ferrule and sutures combination of FIG. 5A after the first and second sutures have been joined by the second system.

With reference now to FIGS. 5A and 5B, an alternate system and method for joining a first length of suture 310 and a second length of suture 320 is shown generally as suture joining system 300. Suture joining system 300 is substantially similar in form and function to suture joining system 200, and will therefore, only be described as relates to the differences therebetween. Suture joining system 300 includes a base 302 having semi-circular recess 303 and a die 304 having a corresponding semi-circular recess 305. Recesses 303, 305 are configured to receive and form the combination of ferrule 320 and first and second suture lengths 310, 330 therein during the welding process.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. Although specific features of the embodiments are shown in some drawings and not in others, this is for convenience only as each feature may be combined with any or all of the other features in accordance with the disclosure. For example, multiple lengths of the same or different sutures may be joined together to form a single suture having multiple segments of the same or different characteristics.

What is claimed is:

1. An apparatus for joining a first length of suture with a second length of suture, the apparatus comprising:
    a substantially cylindrical body have a first end and a second end;
    a first cavity formed in the first end for receiving an end of the first length of suture; and
    a second cavity formed in the second end for receiving an end of the second length of suture, wherein the cylindrical body includes at least one barb extending into at least one of the first and second cavities configured to more securely retain the ends of the first and second lengths of suture therein.

2. The apparatus of claim 1, wherein the first and second cavities include similar diameters.

3. The apparatus of claim 1, wherein the first and second cavities include different diameters.

4. The apparatus of claim 1, wherein the first and second cavities are separated by a divider.

5. The apparatus of claim 1, wherein the first and second cavities are continuous.

6. The apparatus of claim 1, wherein the end of the first length of suture abuts the end of the second length of suture within the cylindrical body.

7. The apparatus of claim 1, wherein the first and second lengths of suture are welded within the respective first and second cavities using one of contact heating and radiant heating.

8. The apparatus of claim 1, wherein the first and second lengths of suture are welded within the respective first and second cavities using ultrasonic welding.

9. The apparatus of claim 1, wherein the cylindrical body is configured to be compressed about the ends of the first and second lengths of suture received within the respective first and second cavities.

10. The apparatus of claim 1, wherein the cylindrical body includes at least one barb extending into the first and second cavities configured to more securely retain the ends of the first and second lengths of suture therein.

11. The apparatus of claim 1, wherein the at least first length of suture is monofilament.

12. The apparatus of claim 1, wherein the at least second length of suture is multifilament.

13. The apparatus of claim 1, wherein at least one of the first and second ends of the substantially cylindrical body are tapered.

14. The apparatus of claim 1, wherein each of the first and second ends of the substantially cylindrical body are tapered.

15. The apparatus of claim 1, wherein the substantially cylindrical body includes a longitudinal gap extend a length thereof.

16. The apparatus of claim 1, wherein at least one of the first and second sutures includes a needle on a second end thereof.

\* \* \* \* \*